United States Patent
Hecht et al.

(10) Patent No.: US 6,833,425 B1
(45) Date of Patent: Dec. 21, 2004

(54) FILLER FOR PLASTIC FORMULATIONS BASED ON POLYURETHANE

(75) Inventors: Reinhold Hecht, Inning-Buch (DE); Bernd Gangnus, Andechs (DE); Günther Lechner, Wörthsee (DE)

(73) Assignee: 3M ESPE AG, Seefeld (DE)

(*) Notice: Subject to any disclaimer, the term of this patent is extended or adjusted under 35 U.S.C. 154(b) by 217 days.

(21) Appl. No.: 10/069,884

(22) PCT Filed: Sep. 1, 2000

(86) PCT No.: PCT/EP00/08569

§ 371 (c)(1),
(2), (4) Date: Jun. 13, 2002

(87) PCT Pub. No.: WO01/18085

PCT Pub. Date: Mar. 15, 2001

(30) Foreign Application Priority Data

Sep. 2, 1999 (DE) .......................................... 199 41 738

(51) Int. Cl.[7] .............................................. C08G 18/62
(52) U.S. Cl. .......................... 528/71; 525/455; 528/75; 524/840; 526/301; 523/115; 523/116; 522/135; 522/141; 522/149

(58) Field of Search ............................. 525/455; 528/71, 528/75; 524/840; 526/301; 523/115, 116; 522/135, 141, 149

(56) References Cited

U.S. PATENT DOCUMENTS

| 4,553,940 A | 11/1985 | Koblitz et al. |
| 4,946,901 A | 8/1990 | Lechner et al. |
| 5,135,963 A | 8/1992 | Haeberle |
| 5,684,081 A | 11/1997 | Dannhorn et al. |

FOREIGN PATENT DOCUMENTS

| DE | 196 17 876 A1 | 11/1997 |
| DE | 197 06 064 A1 | 8/1998 |
| EP | 270 915 | 6/1988 |
| EP | 0 872 502 A1 | 10/1998 |

*Primary Examiner*—Rachel Gorr
(74) *Attorney, Agent, or Firm*—Birch, Stewart, Kolasch & Birch, LLP

(57) ABSTRACT

The invention relates to fillers for plastics formulations based on polyurethane and the use thereof.

15 Claims, No Drawings

FILLER FOR PLASTIC FORMULATIONS BASED ON POLYURETHANE

This application is the national phase under 35 U.S.C. § 371 of PCT International Application No. PCT/EP00/08569 which has an International filing date of Sep. 1, 2000, which designated the United States of America.

The invention relates to fillers for plastics formulations based on polyurethane. The invention relates in particular to organic, crosslinked, reactive and radiation-curing plastics fillers based on polyurethane.

Fillers for use as the filler content of plastics formulations for the purpose of improving the physical properties thereof are sufficiently known. Organic fillers have been used for a long time for dental materials, for example, in addition to inorganic fillers such as quartz or glasses. Bead-shaped polymers and copolymers based on methyl methacrylate are a widely used representative for this.

In addition to bead-shaped polymers, for example, precipitation polymers formed from acrylic acid and/or methacrylic acid esters for use in the dental sector are known from EP-B-0 270 915.

Advantageous features of the use of organic fillers are, inter alia, the easy polishability of the composite materials produced therefrom, the favourable price compared with inorganic fillers ground to an ultrafine degree, the high transparency of the polymers obtained and the ash-free combustibility. Because of the wide variability in the composition which organic fillers can have, material properties can also be influenced in a controlled manner, for example the impact strength of dental materials can be influenced favourably by the graft copolymers mentioned in DE-A1-196 178 76.

Bead-shaped polymers and copolymers based on methyl methacrylate show a high tendency to swell. This is necessary in order to enable partial dissolving of the fillers by monomers, since binding of the fillers to the resin matrix becomes possible only by the formation of an interpenetrating network which takes place during the polymerization. However, a constant increase in the viscosity of the compositions formulated with the fillers is caused by this tendency to swell. In the case of prosthesis plastics, which as a rule comprise the highly solubilizing methyl methacrylate as a main constituent of the monomer matrix, these swelling properties determine, for example, the processing time in the pack-press technique (flask technique). The swelling properties can be measured, for example, by measuring the processing time as described in the international standard ISO 1567, a time frame of approx. 30 to 60 minutes being regarded as usable.

DE-C2-197 060 64 describes plastically curable one-component compositions based on PMMA beads and higher molecular weight crosslinking methacrylates. Although storage stabilities of 6 months are claimed, stiffening of the paste nevertheless already occurs within a few days at slightly elevated temperature (36° C.), this being attributable to the increase in viscosity caused by the partial dissolving of the PMMA beads.

Although the precipitation polymers known from EP-B-0 270 915 are not partially dissolved by the conventional (meth)acrylate monomers of dental technology because of their high crosslinking density and therefore also show no changes in viscosity in the course of storage, they are nevertheless not incorporated particularly well into the resin matrix in spite of the residual double bonds present, so that the resulting composite materials have only moderate mechanical properties. The accessibility of the residual double bonds is evidently ensured to only a limited degree.

Other organic fillers, such as plastics powders ground at room temperature or cryogenically, or precipitated polymer powders, show similar problems.

The fillers based on polyethylene, polypropylene, an ethylene-acrylic acid-acrylic acid ester terpolymer or polyurethane which are commercially obtainable under the trade name "Coathylene" result in composite materials with very inadequate mechanical strengths, since no bonding to the resin matrix is possible because of a lack of reaction centres.

There is therefore a considerable demand for fillers on an organic basis which can be polymerized into the matrix and the swelling properties of which in the conventional monomer matrices of dental technology are so low that formulations with stable viscosity properties even at elevated temperature and over a relatively long storage time can be realized.

The object of the present invention is to provide organic fillers which can satisfy the above-mentioned requirements.

This object is achieved by organic, crosslinked, reactive and radiation-curing plastics fillers based on polyurethane.

The fillers according to the invention have a high reactivity, without undergoing severe swelling in conventional dental monomers. They can be polymerized into resin matrices via ethylenic double bonds, are easy and inexpensive to synthesize, and their properties can be adjusted within a wide range by variation of the educts. They can be radiation-cured via the unsaturated functionalities and are therefore particularly suitable for use in the dental sector, but also in other industrial fields where the properties of the fillers according to the invention are of advantage.

The fillers according to the invention are obtainable by reaction of:

(A) 15 to 35 wt. %, preferably 20 to 30 wt. % of one or more radiation-curing (meth)acrylate-based compounds with OH numbers of 40 to 700 mg KOH/g, (B) 15 to 40 wt. %, preferably 20 to 35 wt. % of one or more polyols with a molecular weight of 500 to 6,000 g/mol, (C) 0 to 15 wt. %, preferably 0 to 10 wt. % of one or more polyols with a molecular weight of less than 500 g/mol, (D) 1 to 10 wt. %, preferably 1 to 7 wt. % of at least one compound which is mono- and/or difunctional in the sense of the isocyanate reaction, which additionally contains anionic groups or functional groups which can be converted into anionic groups, (E) 24 to 69 wt. %, preferably 34 to 55 wt. % of one or more polyisocyanates, and subsequent chain lengthening or crosslinking of the resulting product from (A) to (E) with (F) 0.5 to 10 wt. %, preferably 0.5 to 5 wt. %, relative to the total weight of components (A) to (E), of a mixture of one or more diamines with a polyamine of functionality greater than 2,
at least 30 wt. %, preferably at least 50 wt. % of component (F) comprising polyamine of functionality greater than 2.

Radiation-curing but aqueous dispersions of a similar composition are known from the coatings industry. DE-A-195 25 489 and DE-A44 34 554 describe, for example, polyester-(meth)acrylate-urethane dispersions based on polyester-meth)acrylate prepolymers containing hydroxyl groups. These are obtainable by polyaddition of polyester-(meth)acrylate prepolymers containing hydroxyl groups and compounds which are reactive towards isocyanate groups with polyisocyanates and subsequent reaction with polyfunctional amines. These aqueous dispersions form films on drying, and thus no solid particles which can be used as a filler.

Surprisingly, however, it has been found that by reaction of the above-mentioned components (A) to (E) with subsequent crosslinking by component (F), the fillers according to the invention are obtained after stripping off the solvent. It is particularly advantageous here that after the crosslinking with (F) the fillers can be obtained without additional working-up steps.

Component (A) comprises radiation-curing (meth) acrylate-based compounds which have OH numbers from 40 to 700 mg KOH/g according to DIN 53 240. The term (meth)acrylate is used in this specification to represent methacrylate and/or acrylate.

Suitable components (A) are, for example, polyester-(meth)acrylate prepolymers containing hydroxyl groups such as are described in U.S. Pat. No. 4,206,205, DE-OS40 40 290, DE-OS-33 16 592, DE-OS-37 04 098 and in "UV & EB Curing Formulations for Printing Inks Coatings and Paints", ed. R. Holman and P. Oldring, published by SITA Technology, London (England) 1988, p. 36 et seq. Alternatively, polyepoxy(meth)acrylate prepolymers containing hydroxyl groups which are accessible by reaction of polyepoxides with (meth)acrylic acid, and/or polyurethane-(meth)acrylate prepolymers containing hydroxyl groups can also be used. The use of polyepoxy(meth)acrylate prepolymers containing hydroxyl groups, such as 2,2-bis-4-(3-methacryloxy-2-hydroxypropyl)phenylpropane (bis-GMA), 2,2-bis-4-(3-acryloxy-2-hydroxypropyl)phenylpropane (bis-GA), and of (meth)acrylate esters containing hydroxyl groups, such as glycerol mono(meth)acrylate, trimethylolpropane mono(meth)acrylate or pentaerythritol di(meth) acrylate, is particularly preferred.

Polyols of component (B) have a molecular weight of 500 to 6,000 g/mol and can be in a linear or slightly branched form. The polyols can be taken from the known chemical classes of polymeric polyols which are used in polyurethane syntheses or formulations. Examples which may be mentioned are polyester-, polyester-amide-, polyether-, polythioether-, polycarbonate-, polyacetal-, polyolefin-, polysiloxane- and poly(meth)acrylate-polyols.

The polyester-polyols are reaction products of low molecular weight polyols with low molecular weight polycarboxylic acids.

Suitable low molecular weight polyols or polyol mixtures are, for example, ethylene glycol, propylene glycol, 1,4-butanediol, 1,6-hexanediol, diethylene glycol, triethylene glycol, neopentylglycol, 1,4-bis(hydroxymethyl)-cyclohexane, dipropylene glycol. Glycerol, trimethylolpropane or pentaerythritol, for example, are suitable as polyols of higher functionality, a proportion of which can be co-used to introduce branchings into the polyester molecule. 1,6-hexanediol, neopentylglycol and trimethylolpropane are particularly preferred.

The low molecular weight polycarboxylic acids can be aliphatic, cycloaliphatic, aromatic and/or heterocyclic in nature. Instead of the free polycarboxylic acids, it is also possible to use corresponding polycarboxylic acid anhydrides or polycarboxylic acid esters with lower alcohols. Examples which may be mentioned are: succinic acid, adipic acid, sebacic acid, azelaic acid, phthalic acid, isophthalic acid, phthalic anhydride, tetrahydrophthalic anhydride, glutaric anhydride, maleic acid, maleic anhydride, fumaric acid and dimethyl terephthalate. Adipic acid is particularly preferred.

Suitable polyester polyols are obtainable from Bayer under the name "Desmophen".

Polyesters which are accessible by polymerization of lactones, such as caprolactone, in combination with a polyol can also be used. Polyester-amide-polyols can be obtained by using a proportion of amino-alcohols, such as ethanolamine, in the polyester formation mixture.

Polyether-polyols which can be used comprise products which are accessible by polymerization of a cyclic oxide, for example ethylene oxide, propylene oxide or tetrahydrofuran, or by addition of one or more of these oxides to polyfunctional initiators, such as water, ethylene glycol, propylene glycol, diethylene glycol, cyclohexanedimethanol, glycerol, trimethylolpropane, pentaerythritol or bisphenol A. Particularly suitable polyether polyols are polyoxypropylenediols and -triols, poly(oxyethylene-oxypropylene)diols and -triols, which are obtained by simultaneous or successive addition of ethylene and propylene oxide to suitable initiators, and polytetramethylene ether glycols, which are formed by polymerization of tetrahydrofuran.

Polythioether-polyols which can be used are, inter alia, products which are obtained by condensation of thiodiglycol by itself or with other glycols, dicarboxylic acids, formaldehyde, amino-alcohols or aminocarboxylic acids.

Polycarbonate-polyols which can be used are, inter alia, products which result by reaction of diols, such as 1,3-propanediol, 1,4-butanediol, 1,6-hexanediol, diethylene glycol or tetraethylene glycol, with diaryl carbonates, such as diphenyl carbonate, or with phosgene.

Suitable polyacetal-polyols are compounds which can be prepared by reaction of glycols, such as diethylene glycol, triethylene glycol or 1,6-hexanediol, with formaldehyde or by polymerization of cyclic acetals.

Suitable polyolefin-polyols are, inter alia, butadiene homo- and copolymers with terminal hydroxyl groups.

Suitable polysiloxane-polyols are marketed, for example, by Goldschmidt under the name "Tegomer HSi".

Suitable poly(meth)acrylate-polyols are obtainable, for example, from Tego under the name "Tegodiol".

Polyester-polyols and polycarbonate-polyols with a molecular weight of 500 to 6,000 g/mol, and in particular with a molecular weight of 500 to 3,000 g/mol, are particularly preferred as component (B). Such compounds are commercially obtainable, for example, from Daicel under the name "Placcel".

Suitable polyols of component (C) with a molecular weight of less than 500 g/mol are the following: aliphatic, cycloaliphatic, aromatic and/or heterocyclic compounds such as have already been mentioned substantially for component (B) in the context of the description for building up the polyester-polyols. Particularly preferred polyols of component (C) are neopentylglycol and trimethylolpropane.

Component (D) is, for example, at least one hydroxycarboxylic acid and/or aminocarboxylic acid and/or aminosulphonic acid and/or hydroxysulphonic acid. These compounds are incorporated into the prepolymer, which results from components (A) to (E) in the end, via the amino and/or hydroxy groups which are reactive towards the isocyanates of component (E). The compounds of component (D) acquire dispersing properties by neutralization of the carboxyl groups and/or sulphonic acid groups with organic and/or inorganic bases.

Examples which may be mentioned as representative of component (D) are: malic acid, glycolic acid, glycine, taurine, aminocaproic acid and 2-aminoethylaminosulphonic acid. The preferred representatives of component (D) include 2,2-bis hydroxymethyl) alkanemonocarboxylic acids with a total of 5 to 8 carbon atoms according to the general formula(1):

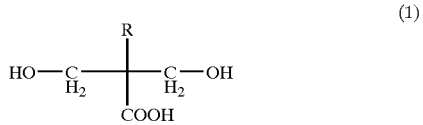

in which R represents a linear, branched or cyclic alkyl radical with 1 to 7 C atoms. 2,2-dimethylolpropionic acid is a vary particularly preferred builder component (D).

Polyisocyanates which are suitable as component (E) are aliphatic, cycloaliphatic and/or aromatic in nature.

Examples of suitable polyisocyanates are: 1,6-hexamethylene diisocyanate (HDI), tetramethylene diisocyanate, isophorone diisocyanate, 4,4'-dicyclohexylmethane diisocyanate, 1,4-phenylene diisocyanate, 2,6- and 2,4-toluene diisocyanate, 1,5-naphthylene diisocyanate, 2,4'- and 4,4'-diphenylmethane diisocyanate. It is of course also possible to use or to co-use a proportion of the polyisocyanates of higher functionality which are known per se in polyurethane chemistry, or also of modified polyisocyanates, for example containing carbodiimide groups, allophanate groups, isocyanurate groups, urethane groups and/or biuret groups which are known per se. Particularly preferred isocyanates are cycloaliphatic isocyanates, such as isophorone diisocyanate and 4,4'-dicyclohexylmethane diisocyanate.

Components (A) to (E) are initially introduced into a reactor or metered in individually and reacted under anhydrous conditions in a temperature range from 30° C. to 130° C. to give an NCO-containing prepolymer. The equivalent ratio of isocyanate groups to compounds which are reactive towards isocyanate groups is 1.1:1 to 3:1, preferably 1.5:1 to 2:1. Carboxyl groups which are introduced into the prepolymer, for example, by co-using 2,2-dimethylolpropionic acid are not taken into account in the calculation of the equivalent ratio. The isocyanate polyaddition reaction can be carried out in the presence of catalysts which are known in polyurethane chemistry, such as organotin compounds. It is furthermore possible to use an organic solvent before, during or after the prepolymer preparation in order to control the viscosity.

Suitable solvents are, for example, acetone, 2-butanone, tetrahydrofuran, dioxane, dimethylformamide, N-methyl-2-pyrrolidone (NMP), ethyl acetate, alkyl ethers of ethylene glycol and propylene glycol and aromatic hydrocarbons. The use of water-miscible, low-boiling solvents, such as acetone, which can be removed by distillation from the polyurethane-polyurea dispersions prepared, is particularly preferred.

Before dispersion of the prepolymer prepared from components (A) to (E) in water and chain lengthening or crosslinking with component (F), the potential ionic groups present in the prepolymer are converted into ionic groups, for example by neutralization. Tertiary amines are preferably used for the neutralization, in particular if builder components (D) which contain carboxyl groups are used. Such tertiary amines are, for example, triethylamine, tri-n-butylamine, N-methymorpholine, N,N-dimethylethanolamine, N-methylpiperidine, N-methylpiperazine and triethanolamine. The use of inorganic bases, such as sodium hydroxide or potassium hydroxide, as the neutralizing agent is also possible, although less preferred. It is also possible for component (D) already to be used in the neutralized form in the preparation of the prepolymer.

The formation of stable aqueous dispersions is ensured by neutralization of the potential ionic groups. In general, at least 80%, but preferably 100% of the potential ionic groups are converted into ionic groups by neutralization. The neutralization reaction is as a rule carried out here at temperatures below 100° C., and preferably in the temperature range from 30 to 80° C.

The conversion of the neutralized NCO-containing prepolymers into aqueous dispersions is carried out by the methods known in polyurethane chemistry. One possibility is the addition of the dispersing water, which contains component (F), to the prepolymer. In this process, the organic prepolymer initially forms the continuous phase. On further addition of water a phase inversion takes place and the water becomes the continuous phase.

In another dispersing possibility, the neutralized prepolymer is added to the dispersing water. Component (F) can be initially introduced here in the dispersing water, or alternatively can be added only after dispersing of the prepolymer.

The dispersing step is preferably carried out in a temperature range from 20 to 40° C. The dispersibility of the prepolymers in water can be improved here by the additional use of external emulsifiers. Suitable external emulsifiers are, for example, alkyl sulphates, for example with a chain length of 8 to 18 C atoms, and aryl and alkyl ether-sulphates with 8 to 18 C atoms in the hydrophobic radical and 1 to 40 ethylene oxide (EO) or propylene oxide (PO) units.

It is furthermore possible to use:

sulphonates, for example alkylsulphonates with 8 to 18 C atoms, alkylarylsulphonates with 8 to 18 C atoms, esters and half-esters of sulphosuccinic acid with monohydric alcohols or alkylphenols with 4 to 15 C atoms, it also being possible for the alcohols or alkylphenols to be ethoxylated with 1 to 40 EO units, alkali metal and ammonium salts of carboxylic acids, in particular with 8 to 20 C atoms in the alkyl, aryl, alkaryl or aralkyl radical, phosphoric acid partial esters and alkali metal and ammonium salts thereof, for example alkyl and alkaryl phosphates with 8 to 20 C atoms in the organic radical, alkyl ether- or alkaryl ether-phosphates with 8 to 20 C atoms in the alkyl or alkaryl radical and 1 to 40 EO units, alkyl polyglycol ethers with 2 to 40 EO units and alkyl radicals from 4 to 20 C atoms, alkylaryl polyglycol ethers with 2 to 40 EO units and 8 to 20 C atoms in the alkyl and aryl radicals, ethylene oxide/propylene oxide (EO/PO) block copolymers with 8 to 40 EO or PO units, fatty acid polyglycol esters with 6 to 24 C atoms and 2 to 40 EO units and alkyl polyglycosides.

The alkyl radicals can be, for example, in each case branched, unbranched or cyclic in nature or can have a mixture of these features.

Component (F) describes mixtures of one or more diamines with one or more polyamines of functionality greater than 2. The diamines lead to a chain lengthening and therefore to a build up in the molecular weight of the prepolymer, while the polyamine with a functionality greater than 2 effects a crosslinking of the molecular structure. The reaction of the prepolymer with the constituents of component (F) takes place in an aqueous medium. The compounds of component (F) therefore preferably have a higher reactivity towards isocyanate groups compared with water. The amount of component (F) to be used depends on the unreacted isocyanate groups of the prepolymer still present. The isocyanate content of the prepolymer is determined in accordance with DIN 53 185.

Suitable diamines which may be mentioned by way of example are: 1,2-diaminoethane, 1,6-diaminohexane, piperazine, 2,5-dimethylpiperazine, 1-amino-3-aminoethyl-3,5,5-trimethylcyclohexane, 4,4'-diaminodicyclohexylmethane, 1,4-diaminocyclohexane and/or 1,2-propylenediamine. Hydrazine, amino acid hydrazides, bishydrazides and bis-semicarbazides are also suitable as chain lengtheners. 1,2-diaminoethane is a particularly preferred diamine.

Examples of polyamines with a functionality greater than 2 are diethylenetriamine, triethylenetetramine, tetraethylenepentamine, pentaethylenehexamine, polyethyleneimines and melamine. The use of diethylenetriamine is particularly preferred.

The filler according to the invention is present in the solution in dispersed form for example in a concentration of 20 to 60 wt. %, in particular between 25 and 45 wt. %. The pure filler can be obtained by stripping off the solvent, for example by means of a vacuum or also by spray drying. Another possibility for isolating the filler from the aqueous dispersion is by coagulation of the dispersion by means of the addition of salt or by addition of polar solvents. Spray drying is particularly preferred, since the fillers according to the invention are obtained in a small particle size in this process and can be used directly in further formulations.

The fillers according to the invention are particularly suitable for the preparation of dental compositions. Such formulations preferably comprise the following components:

(C1) 1 to 40 wt. %, in particular 5 to 30 wt. % of filler according to the invention, (C2) 10 to 98.9 wt. %, in particular 14 to 94.9 wt. % of one or more ethylenically unsaturated polymerizable monomers based on di- or polyfunctional (meth) acrylates, (C3) 0 to 75 wt. %, in particular 0 to 50 wt. % of conventional fillers, (C4) 0.1 to 3 wt. %, in particular 0.1 to 2 wt. % of initiators and, where appropriate, activators, (C5) 0 to 10 wt. %, in particular 0 to 5 wt. % of additives, where appropriate pigments, thixotropy auxiliaries, plasticizers.

The compositions formulated from the fillers according to the invention are distinguished by particularly good mechanical properties and considerable handling advantages. Because of the good viscoelasticity they are thus particularly hard, but at the same time flexible. The reactive (meth)acrylate groups enable bonding of the fillers into the matrix of the formulation. Due to the high molecular weights the fillers have a maximum biocompatibility and have no toxicologically unacceptable properties at all. With suitable choice of the educts, the formulations burn virtually ash-free.

At least bifunctional acrylic acid and/or methacrylic acid esters are used as component (C2). These can be monomeric and polymeric acrylates and methacrylates. For example, the long-chain monomers of U.S. Pat. No. 3,066,112 based on bisphenol A and glycidyl methacrylate or derivatives thereof formed by addition of isocyanates can advantageously be used. Compounds of the type bisphenol A diethyloxy(meth) acrylate and bisphenol A dipropyloxy(meth)acrylate are also suitable. The oligo-ethoxylated and oligo-propoxylated bisphenol A diacrylic and dimethacrylic acid esters can furthermore be used.

The acrylic acid and methacrylic acid esters of at least bifunctional aliphatic alcohols are also particularly suitable, for example triethylene glycol di(meth)acrylate, ethylene glycol di(meth)acrylate, hexanediol di(meth)acrylate and trimethylolpropane tri(meth)acrylate.

The diacrylic and dimethacrylic acid esters of bis (hydroxymethyl)-tricyclo[$5.2.1.0^{2,6}$]-decane, which are mentioned in DEC-28 16 823, and the diacrylic and dimethacrylic acid esters of bis(hydroxymethyl)-tricyclo [$5.2.1.0^{2,6}$]-decane compounds lengthened with 1 to 3 ethylene oxide and/or propylene oxide units are also particularly suitable.

The methacrylic acid esters described in EP-A-0 235 826, for example triglycolic acid bis[3(4)-methacryloxymethyl-8(9)-tricyclo[$5.2.1.0^{2,6}$]-decylmethyl ester], are also particularly suitable monomers.

Mixtures of monomers and/or of unsaturated polymers prepared therefrom can of course also be used.

Conventional fillers according to component (C3) can be inorganic fillers, for example quartz, ground glasses, fluorides which are not water-soluble, such as $CaF_2$, silica gels and silica, in particular pyrogenic silica or granules thereof. For better incorporation into the matrix it may be advantageous to hydrophobize these fillers and, if appropriate, additives which are opaque to x-rays. In a preferred embodiment, all the inorganic fillers used are silanized, preferably with trimethoxymethacryloxypropylsilane. The amount of silane used is usually 0.5 to 10 wt. %, relative to the inorganic fillers, preferably 1 to 6 wt. %, very particularly preferably 2 to 5 wt. %, relative to the inorganic fillers. Conventional hydrophobizing agents are silanes, for example trimethoxymethacryloxypropylsilane. The maximum average particle size of the inorganic fillers is preferably 15 μm, in particular 8 μm. Fillers with an average particle size of <3 μm are very particularly preferably used.

Fillers which release fluoride, for example complex inorganic fluorides from DE-A-44 45 266, can also be used.

Conventional bead-shaped polymers and copolymers based on methyl methacrylate, which are obtainable, for example, from Röhm under the name "Piexidon" or "Plex" can furthermore also be used.

By initiators of component (C4) are meant initiator systems which effect radical polymerization of the at least bifunctional monomers, for example photoinitiators or so-called redox initiator systems, but also thermal initiators.

Suitable photoinitiators are, for example, α-diketones, such as camphorquinone, in combination with secondary and tertiary amines, or mono- and bisacylphosphine oxides, such as 2,4,6-trimethylbenzoyidiphenyl-phosphine oxide and bis-(2,6-dichlorobenzoyl)-4-n-propylphenyl-phosphine oxide. However, other compounds of this type such as are described in the European Patent specification publications EP-A-0 073 413, EP-A-0 007 508, EP-A-0 047 902, EP-A-0 057 474 and EP-A-0 184 095 are also suitable.

Suitable redox initiator systems are organic peroxide compounds together with so-called activators. Possible organic peroxide compounds here are, in particular, compounds such as lauroyl peroxide, benzoyl peroxide and p-chlorobenzoyl peroxide and p-methylbenzoyl peroxide.

Suitable activators are, for example, tertiary aromatic amines, such as the N,N-bis-(hydroxyalkyl)-3,5-xylidines known from U.S. Pat. No. 3,541,068 and the N,N-bis-(hydroxyalkyl)-3,5-di-t-butylanilines known from DE-A-26 58 530, in particular N,N-bis-(β-oxybutyl)-3,5-di-t-butylaniline and N,N-bis-(hydroxyalkyl)-3,4,5-trimethylanilines.

The barbituric acids and barbituric acid derivatives described in DE-B-14 95 520 and the malonylsulphamides described in EP-A-0 059 451 are also particularly suitable activators. Preferred malonylsulphamides are 2,6-dimethyl-4-isobutylmalonylsulphamide, 2,6-diisobutyl-4-propylmalonylsulphamide, 2,6-dibutyl-4-propylmalonylsulphamide, 2,6-dimethyl-4-ethylmalonylsulphamide and 2,6-dioctyl-4-isobutylmalonylsulphamide.

For further acceleration, the polymerization is preferably carried out here in the presence of heavy metal compounds and ionic halogen or pseudohalogen. Copper is particularly suitable as the heavy metal and the chloride ion as the halide. The heavy metal is suitably used in the form of soluble organic compounds. The halide and pseudohalide ions are also suitably used in the form of soluble salts, and the soluble amine hydrochlorides and quaternary ammonium chloride compounds may be mentioned as examples.

If the dental compositions according to the invention contain a redox initiator system of organic peroxide and activator as component (C4), the peroxide and activator are preferably present in parts of the dental composition according to the invention which are spatially separated from one another and are mixed homogeneously with one another only immediately before the use of the dental composition according to the invention. If the dental composition according to the invention contains as (C4) organic peroxide, copper compound, halide and malonylsulphamide and/or barbituric acid side by side, it is particularly useful for the organic peroxide, malonylsulphamide and/or barbituric acid and the combination of copper compound/halide to be present in three constituents which are spatially separated from one another. For example, the combination of copper compound/halide, polymerizable monomers and fillers can be kneaded to a paste and the other components can be kneaded to two separate pastes in the manner described above in each case with a small amount of fillers or, in particular, thixotropy auxiliaries, such as silanized silica, and a plasticizer, for example phthalate. On the other hand, the polymerizable monomers can also be present together with organic peroxide and fillers.

Soluble organic polymers can be used as component (C5), for example, to increase the flexibility of the compositions. Suitable polymers are, for example, polyvinyl acetate and copolymers based on vinyl chloride/vinyl acetate, vinyl chloride/vinyl isobutyl ether and vinyl acetate/maleic acid dibutyl ether. Dibutyl, dioctyl and dinonyl phthalates or adipates and higher molecular weight polyphthalic acid esters and adipic acid esters are particularly suitable as additional plasticizers. In addition to pyrogenic silicas, modified laminar silicates (bentonites) or organic modifying agents, for example based on hydrogenated castor oil derivatives, can also be used as thixotropy auxiliaries.

Dental materials which comprise the fillers according to the invention can be, for example, filling materials, cements, temporary crown and bridge materials, veneer plastics, prosthesis materials, orthodontic materials, plastics for sealing fissures, modelling plastics or model plastics.

The fillers according to the invention are also suitable for use in formulations for gluing, coating and embedding substrates, for example as a filler for stopper compositions or for improvements to the properties of plastics in general.

The invention is described in more detail in the following by examples, without limiting it.

Polyurethane Filler

PREPARATION EXAMPLE 1

A 2 l 3-necked flask fitted with a thermometer, reflux condenser and mechanical stirrer was charged with 200 g bis-GMA (component A), 40.2 g dimethylolpropionic acid (component D), 23.1 g 1,6-hexanediol (component C), 195.8 g of a polyester-polyol (component B) prepared from terephthalic acid/neopentylglycol with a molecular weight of 1,000 g/mol, 420 g acetone, 333 g isophorone diisocyanate (component E) and 0.1 g dibutyltin dilaurate. The reaction mixture was heated for 5 hours at 60° C., until the isocyanate content had fallen to 3.9%. The reactor was cooled to 20° C. and the mixture was neutralized with 27.2 g triethylamine.

The prepolymer solution obtained is dispersed in 1,152 g deionized water at 23° C., while stirring, and subsequently crosslinked by addition of 7.0 g ethylenediamine (component F) and 8.0 g diethylenetriamine (component F). After twenty hours the dispersion had a pH value of 7.7 and a solids content of 34.5%.

The dispersion was dried in a thin layer in a drying cabinet at 40° C. The granules obtained were brought to a particle size distribution of 50% <60 $\mu$m, 99% <200 $\mu$m by grinding.

PREPARATION EXAMPLE 2

A 2 l 3-necked flask fitted with a thermometer, reflux condenser and mechanical stirrer was charged with 200 g bis-GMA (component A), 40.2 g dimethylolpropionic acid (component D), 214.5 g ethoxylated bisphenol A (component B) with a molecular weight of 550, 356 g tetrahydrofuran, 333 g isophorone diisocyanate (component E) and 0.1 g dibutyltin dilaurate. The reaction mixture was heated for 5 hours at 60° C., until the isocyanate content had fallen to 3.5%. The reactor was cooled to 20° C. and the mixture was neutralized with 27.2 g triethylamine.

The prepolymer solution obtained is dispersed in 1,296 g deionized water at 23° C., while stirring, and subsequently crosslinked by addition of 9 g ethylenediamine (component F) and 7.8 g diethylenetriamine (component F). After twenty hours the dispersion had a pH value of 7.9 and a solids content of 33.5%.

The dispersion was dried in a thin layer in a drying cabinet at 40° C. The granules obtained were brought to a particle size distribution of 50% <60 $\mu$m, 99% <200 $\mu$m by grinding.

Dental Model Materials

PREPARATION EXAMPLE 3

1. Preparation of a Monomer Solution

The constituents listed in the following table are stirred in a conical flask in a suitable red light room until a homogeneous solution is obtained.

| | |
|---|---|
| 74.27 g | Bis-GMA stab. with 200 ppm hydroquinone monomethyl ether (HQME) |
| 18.57 g | Bis(hydroxymethyl)-tricyclo[5.2.1.0$^{2,6}$]-decane diacrylate stab. with 100 ppm HQME and 180 ppm Jonol |
| 0.40 g | Bis-(2,6-dichlorobenzoyl)-4-n-propylphenyl-phosphine oxide |
| 6.76 g | Poly(phthalic acid 1,6-hexanediol ester) with a viscosity of 1,200 to 1,300 mPas |

2. Preparation of the Pastes

The pastes described in the following are prepared therefrom using a laboratory kneader. The filler additions are carried out successively, and after each part addition kneading is carried out under reduced pressure (200 mbar) until the paste is homogeneous. The kneading times are between 6 h and 9 h. The amounts data are in percent by weight.

|                        | Com-1 | Com-2 | Com-3 | Com-4 | Com-5 |
|------------------------|-------|-------|-------|-------|-------|
| Monomer solution       | 83%   | 69%   | 69%   | 67%   | 72%   |
| Precipitation polymer# | 17%*  | 13%   | 13%   | 13%   | 13%   |
| PU filler 1            |       |       | 18%   |       |       |
| PU filler 2            |       |       |       | 18%   |       |
| Plex-6690-F            |       |       |       |       | 15%   |
| Coathylene TB 2957     |       |       |       | 20%   |       |

*a higher degree of filling cannot be achieved
according to preparation example 3 of EP-0 270 915

The pastes obtained are kept for 1 day at 50° C. A certain increase in viscosity again took place here in all the pastes.

The pastes prepared in this way show, after curing (photopolymerization apparatus Visio beta vario, ESPE) the mechanical properties listed in the following:

|                              | Com-1 | Com-2 | Com-3 | Com-4 | Com-5 |
|------------------------------|-------|-------|-------|-------|-------|
| Flexural strength [MPa]      | 48    | 77    | 69    | 35    | 27    |
| E modulus [MPa]              | 1,300 | 2,200 | 1,980 | 990   | 1,020 |
| Ball indentation hardness [MPa] | 79 | 100   | 106   | 43    | 41    |

If the pastes obtained are stored a different temperatures, the following observations can be achieved:

| Storage time | Temperature | Com-1 | Com-2 | Com-3 | Com-4 | Com-5 |
|--------------|-------------|-------|-------|-------|-------|-------|
| 1 week       | 4° C.       | OK    | OK    | OK    | OK    | OK    |
|              | 23° C.      | OK    | OK    | OK    | OK    | OK    |
|              | 36° C.      | OK    | OK    | OK    | OK    | stiffened |
| 1 month      | 4° C.       | OK    | OK    | OK    | OK    | OK    |
|              | 23° C.      | OK    | OK    | OK    | OK    | stiffened |
|              | 36° C.      | OK    | OK    | OK    | OK    | —     |
| 6 months     | 4° C.       | OK    | OK    | OK    | OK    | stiffened |
|              | 23° C.      | OK    | OK    | OK    | OK    | —     |
|              | 36° C.      | OK    | OK    | OK    | tacky, rubbery | — |
| 12 months    | 4° C.       | OK    | OK    | OK    | OK    | —     |
|              | 23° C.      | OK    | OK    | OK    | tacky, rubbery | — |
|              | 36° C.      | OK    | OK    | OK    | —     | —     |

Temporary Crown and Bridge Materials

PREPARATION EXAMPLE 4

1. Preparation of a Catalyst Paste

The constituents listed in the table are mixed in a kneader until a homogeneous paste with a viscosity of 78 Pas is obtained. The kneading times are between 4 h and 7.5 h.

| | |
|---|---|
| 38.9 g | acetylated bisphenol A with a degree of ethoxylation of 4 |
| 5 g | poly(phthalic acid 1,6-hexanediol ester) with a viscosity of 1,200 to 1,300 mPas |
| 51 g | SrAlB silicate glass ($d_{50}$ = 10 μm, silanized with 1% 3-methacroylpropoxytrimethoxysilane) |
| 4.1 g | di(4-methylbenzoyl) peroxide |
| 1 g | pyrogenic silica |

2. Preparation of the Base Pastes

The constituents listed in the table are mixed in a kneader until a homogeneous paste with a viscosity of between 8–12 Pas is obtained. The kneading times are between 2.5 h and 4.5 h. The amounts data are in percent by weight.

|                                                                                                          | TCB-1 | TCB-2 |
|----------------------------------------------------------------------------------------------------------|-------|-------|
| 2,2-Bis-(4-di(ethoxy)phenyl)-propane dimethacrylate                                                      | 46.5% | 46.5% |
| 7,7,9-Trimethyl-4,13-dioxo-3,14-dioxa-5,12-diazahexadecane 1,16-dioxydimethacrylate                      | 31%   | 31%   |
| SrAlB silicate glass ($d_{50}$ = 10 μm, silanized with 1% 3-methacroylpropoxytrimethoxysilane)            | 18%   | 13%   |
| PU filler according to example 2                                                                         | 0%    | 5%    |
| Pyrogenic silica                                                                                         | 3%    | 3%    |
| N,N-Bis-(2-hydroxyethyl)-4-methylaniline                                                                 | 1.5%  | 1.5%  |

The pastes prepared in this way are mixed in a ratio of 4:1 (base:catalyst). The cured formulations have the mechanical properties listed in the following:

|                                   | TCB-1 | TCB-2 |
|-----------------------------------|-------|-------|
| Flexural strength [MPa]           | 73    | 71    |
| E modulus [MPa]                   | 1,300 | 1,420 |
| Impact strength [mJ/mm$^2$]       | 3.23  | 5.18  |

What is claimed is:

1. Filler for plastics formulations based on polyurethane, obtained by reaction of the following components (A) to (E):

(A) 15 to 35 wt. % of one or more radiation-curing (meth)acrylate-based compounds with OH numbers of 40 to 700 mg KOH/g (B) 15 to 40 wt. % of one or more polyols with a molecular weight of 500 to 6,000 g/mol (C) 0 to 15 wt. % of one or more polyols with a molecular weight of less than 500 g/mol (D) 1 to 10 wt. % of at least one compound which is mono- and/or difunctional in the sense of the isocyanate reaction, which additionally contains anionic groups or functional groups which can be converted into anionic groups (E) 24 to 69 wt. % of one or more polyisocyanates, and subsequent crosslinking the resulting product from (A) to (E) with component (F)

(F) 0.5 to 10 wt. % relative to the total weight of components (A) to (E), of a mixture of at least one diamine with a polyamine of functionality greater than 2, at least 30 wt. % of component (F) comprising polyamine of functionality greater than 2.

2. Filler according to claim 1, wherein components (A) to (F) are defined as follows:

(A) one or more of the following compounds: polyester-(meth)acrylate prepolymer containing hydroxyl groups, polyepoxy(meth)acrylate prepolymer containing hydroxyl groups, polyurethane-(meth)acrylate prepolymer containing hydroxyl groups and (meth)acrylate ester containing hydroxyl groups, (B) one or more of the following compounds: polyester-, polyester-amide-, polyether-, polythioether-, polycarbonate-, polyacetal-, polyolefin-, polysiloxane- and poly(meth)acrylate-polyols, (C) one or more of the following compounds: ethylene glycol, propylene glycol, 1,4-butanediol, 1,6-hexanediol, diethylene glycol, triethylene glycol, neopentylglycol, 1,4-bis (hydroxymethyl)- cyclohexane, dipropylene glycol, glycerol, trimethylolpropane or pentaerythritol,
(D) one or more of the following compounds: malic acid, glycolic acid, glycine, taurine, aminocaproic acid, 2-amino-ethylaminosulphonic acid, 2,2-bis (hydroxymethyl)-alkanemonocarboxylic acids with a total of 5 to 8 carbon atoms according to the general formula (1):

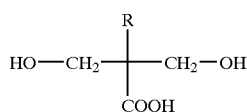

(1)

in which R represents a linear, branched or cyclic alkyl radical with 1 to 7 C atoms,
(E) one or more of the following compounds: 1,6-hexamethylene diisocyanate, tetramethylene diisocyanate, isophorone diisocyanate, 4,4',-dicyclohexylmethane diisocyanate, 1,4-phenylene diisocyanate, 2,6- and 2,4-toluene diisocyanate, 1,5-naphthylene diisocyanate, 2,4'- and 4,4'-diphenylmethane diisocyanate, polyisocyanates of higher functionality or modified isocyanates, such as polyisocyanates containing carbodiimide groups, allophanate groups, isocyanurate groups and/or biuret groups,
(F) one or more of the following compounds: 1,2-diaminoethane, 1,6-diaminohexane, piperazine, 2,5-dimethylpiperazine, 1-amino-3-aminoethyl-3,5,5-trimethylcyclohexane, 4,4'-diaminodicyclohexylmethane, 1,4-diaminocyclohexane, 1,2-propylenediamine, hydrazine, amino acid hydrazides, bishydrazides, bis-semicarbazides and polyamines with a functionality greater than 2.

3. Filler according to claim 1 or 2, wherein components (A) to (F) are defined as follows:
(A) one or more of the following compounds: 2,2-bis-4-(3-methacryloxy-2-hydroxypropyl)phenylpropane, 2,2-bis-4-(3-acryloxy-2-hydroxypropyl) phenylpropane, glycerol monoacrylate, glycerol monomethacrylate, trimethylolpropane monoacrylate, trimethylolpropane monomethacrylate, pentaerythritol diacrylate, pentaerythritol dimethacrylate,
(B) one or more of the following compounds: polyester- and polycarbonate-diols,
(C) one or more of the following compounds: neopentylglycol, trimethylolpropane, 1,6-hexanediol,
(D) 2,2-dimethylolpropionic acid,
(E) isophorone diisocyanate and/or 4,4', dicyclohexylmethane diisocyanate,
(F) as diamine: 1,2-diamionethane; as polyamine with a functionality greater than 2: diethylenetriamine.

4. A dental filling composition comprising the filler as disclosed in claim 1 or 2.

5. A material for the dental filling, dental cementing, temporary crown and bridge materials, veneer plastics, prosthesis materials, orthodontic materials, plastics for sealing fissures, modeling plastics or model plastics wherein said material is comprised of the filler as disclosed in claim 1 or 2.

6. A formulation for coating, gluing or embedding substrates comprising the filler as disclosed in claim 1 or 2.

7. Process for the preparation of fillers for plastics formulations based on polyurethane, comprising the following steps of:
(1) reaction of a mixture of:
(A) 15 to 35 wt. % of one or more radiation-curing (meth)acrylate-based compounds with OH numbers of 40 to 700 mg KOH/g
(B) 15 to 40 wt. % of one or more polyols with a molecular weight of 500 to 6,000 g/mol
(C) 0 to 15 wt. % of one or more polyols with a molecular weight of less than 500 g/mol
(D) 1 to 10 wt. % of at least one compound which is mono- and/or difunctional in the sense of the isocyanate reaction, which additionally contains anionic groups or functional groups which can be converted into anionic groups
(E) 24 to 69 wt. % of one or more polyisocyanates,
(2) neutralization of the potential ionic groups present in the prepolymers;
(3) dispersing in water and crosslinking with:
(F) 0.5 to 10 wt. %, relative to the total composition of components (A) to (E), of a mixture of at least one diamine with a polyamine of functionality greater than 2;
at least 30 wt. % of component (F) comprising polyamine of functionality greater than 2;
(4) working up.

8. A composition comprising the filler according to claim 1 or 2 present in an amount of from 1 to 40 wt. % and further comprising:
(C1) 10 to 98.8 wt. % of one or more ethylenically unsaturated polymerizable monomers based on di- or polyfunctional (meth)acrylates,
(C2) 0 to 75 wt. % of conventional fillers,
(C3) 0.1 to 3 wt. % of initiators,
(C4) 0 to 10 wt. % of additives, and
optionally containing one or more members selected from the group consisting of activators pigments, thixotrophy auxiliaries, and plasticizers.

9. The filler according to claim 1, wherein at least 50 wt. % of component (F) is a polyamine having a functionality greater than 2.

10. A method of manufacturing a member selected from the group consisting of filling materials, cements, temporary crown and bridge materials, veneer plastics, prosthesis materials, orthodontic materials, plastics for sealing fissures, modeling plastics and model plastics wherein said method comprises the steps of reacting the components (A) to (E) and subsequently crosslinking the resulting product from (A) to (E) with component (F) according to claim 3.

11. A composition comprising the filler according to claim 3 present in an amount of from 1 to 40 wt. % and further comprising:
(C1) 10 to 98.8 wt. % of one or more ethylenically unsaturated polymerizable monomers based on di- or polyfunctional (meth)acrylates,
(C2) 0 to 75 wt. % of conventional fillers,
(C3) 0.1 to 3 wt. % of initiators,
(C4) 0 to 10 wt. % of additives,
and optionally containing one or more members selected from the group consisting of activators pigments, thixotrophy auxiliaries, and plasticizers.

12. An article of manufacture comprising the filler according to claim 1 or 2 in cured form.

13. An article of manufacture comprising the filler according to claim 3 in cured form.

14. The article of manufacture according to claim 12 wherein the article of manufacture is selected from the group consisting of a filling, cement, temporary crown, a temporary bridge material, veneer plastic, prosthesis, orthodontic appliance, plastic seal and a plastic model.

15. The article of manufacture according to claim 13 wherein the article of manufacture is selected from the group consisting of a filling, cement, temporary crown, a temporary bridge material, veneer plastic, prosthesis, orthodontic appliance, plastic seal and a plastic model.

* * * * *

UNITED STATES PATENT AND TRADEMARK OFFICE
CERTIFICATE OF CORRECTION

PATENT NO. : 6,833,425 B1
DATED : December 21, 2004
INVENTOR(S) : Hecht, Reinhold It is certified that error appears in the above-identified patent and that said Letters Patent is hereby corrected as shown below:

Column 2,
Line 58, delete "DE-A44 34 554" and insert -- DE-A-44 34 554 -- therefor.
Line 60, after "polyester-" insert -- ( --.

Column 3,
Lines 15-16, delete "DE-OS40  40  290" and insert -- DE-OS-40 40 290 --, therefor.

Column 4,
Line 61, delete "representative" and insert -- representatives --, therefor.
Line 65, after "bis" insert -- ( --.

Column 5,
Line 10, delete "vary" and insert -- very --, therefor.

Column 7,
Line 48, delete "considerablc" and insert -- considerable --, therefor.

Column 8,
Line 8, delete "DEC-28 16 823" and insert -- DE-C-28 16 823 --, therefor.
Line 39, delete "Piexidon" and insert -- Plexidon --, therefor.
Line 48, delete "trimethylbenzoyidiphenyl" and insert -- trimethylbenzoyldiphenyl --, therefor.

UNITED STATES PATENT AND TRADEMARK OFFICE
CERTIFICATE OF CORRECTION

PATENT NO.    : 6,833,425 B1
DATED         : December 21, 2004
INVENTOR(S)   : Hecht, Reinhold It is certified that error appears in the above-identified patent and that said Letters Patent is hereby corrected as shown below:

<u>Column 13,</u>
Lines 20 and 53, delete "4,4'," and insert -- 4,4' --, therefor.
Line 59, after "for" delete "the".

Signed and Sealed this

Twenty-third Day of August, 2005

JON W. DUDAS
*Director of the United States Patent and Trademark Office*